United States Patent
Mondet et al.

(10) Patent No.: US 6,949,504 B2
(45) Date of Patent: Sep. 27, 2005

(54) COMPOSITION COMPRISING AT LEAST ONE LIQUID FATTY PHASE STRUCTURED BY AT LEAST ONE SEMI-CRYSTALLINE POLYMER

(75) Inventors: Jean Mondet, Aulnay Sous Bois (FR); Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 147 days.

(21) Appl. No.: 10/138,327

(22) Filed: May 6, 2002

(65) Prior Publication Data

US 2002/0197220 A1 Dec. 26, 2002

Related U.S. Application Data

(60) Provisional application No. 60/294,978, filed on Jun. 4, 2001.

(30) Foreign Application Priority Data

May 4, 2001 (FR) .............................. 01 06047

(51) Int. Cl.$^7$ ............................ A61K 7/00; A61K 7/27; A06K 7/31; A06K 7/23
(52) U.S. Cl. ...................... 514/1; 514/772.1; 514/788.1; 514/789; 514/844
(58) Field of Search ...................... 514/1, 772.1, 788.1, 514/789, 844

(56) References Cited

U.S. PATENT DOCUMENTS

| | | | |
|---|---|---|---|
| 5,156,911 A | 10/1992 | Stewart | |
| 5,302,380 A | 4/1994 | Castrogiovanni et al. | |
| 5,318,995 A | 6/1994 | Mondet et al. | |
| 5,519,063 A | 5/1996 | Mondet et al. | |
| 5,736,125 A | 4/1998 | Morawsky et al. | |
| 6,180,123 B1 * | 1/2001 | Mondet | 424/401 |

FOREIGN PATENT DOCUMENTS

| | | | |
|---|---|---|---|
| EP | 0 550 745 | 7/1993 | |
| EP | 0 951 897 | 10/1999 | |
| EP | 951897 A2 * | 10/1999 | A61K/7/02 |
| EP | 1 034 776 | 9/2000 | |
| WO | WO 01/19333 | 3/2001 | |
| WO | WO 200119333 A1 * | 3/2001 | A61K/7/00 |

OTHER PUBLICATIONS

English language Derwent Abstract of EP 1 034 776, Sep. 13, 2000.
Shuichi Nojima et al., "Melting Behavior of Poly($\epsilon$–caprolactone)–block–Polybutadiene Copolymers," Macromolecules, vol. 32, No. 11, Jun. 1, 1999, pp. 3727–3734.
B. Boutevin et al., "Study of morphological and mechanical properties of PP/PBT blends," Polymer Bulletin, vol. 34, No. 1, Jan. 1995, pp. 116–123.
Pratima Rangarajan et al., "Morphology of Semicrystalline Block Copolymers of Ethylene–(Ethylene–alt–propylene)," Macromolcule, vol. 26, No. 17, Aug. 16, 1993, pp. 4640–4645.
D Richter et al., "Polymer Aggregates with Crystalline Cores: The System Polyethylene–Poly(ethylenepropylene)," Macromolecules, vol. 30, No. 4, Feb. 24, 1997, pp. 1053–1068.
I.W. Hamley, "Crystallization in Block Copolymers," Advances in Polymer Science, vol. 148, Springer–Verlag Berlin Heidelberg, 1999, pp. 115–137.

* cited by examiner

*Primary Examiner*—Kelechi C. Egwim
(74) *Attorney, Agent, or Firm*—Finnegan, Henderson, Farabow, Garrett & Dunner LLP

(57) ABSTRACT

A composition comprising at least one liquid fatty phase structured by at least one semi-crystalline polymer having a low melting point and an organic structure, wherein said polymer is solid at ambient temperature, has a melting temperature of less than 50° C., and comprises a) a polymer backbone and b) at least one crystallizable organic side chain and/or one crystallizable organic block that forms part of the polymer backbone of said polymer, wherein said polymer has a number-average molecular mass of greater than 2000, and wherein the liquid fatty phase and the polymer form a physiologically acceptable medium. This composition is provided in the form of a stick, for example, which deposits, on keratinous substances such as the lips, a glossy, nonsticky and covering film.

53 Claims, No Drawings

COMPOSITION COMPRISING AT LEAST ONE LIQUID FATTY PHASE STRUCTURED BY AT LEAST ONE SEMI-CRYSTALLINE POLYMER

This application claims benefit of U.S. Provisional Application No. 60/294,978, filed Jun. 4, 2001.

The present invention relates to a composition for caring for and/or treating and/or making up the skin, including the scalp, and/or the lips of the face of human beings, which comprises a liquid fatty phase structured by at least one specific polymer and which is provided, for example, in the form of a stick of lipstick, the application of which results in a glossy covering and nonsticky deposit.

It is commonplace, in cosmetic or dermatological products, to find a structured, namely stiffened, liquid fatty phase. This is particularly the case in solid compositions, such as deodorants, lip balms, lipsticks, concealers and cast foundations.

In accordance with the present invention, the phrase "liquid fatty phase" is understood to mean a fatty phase which is liquid at ambient temperature (25° C.) and atmospheric pressure (760 mm of Hg), and which is composed of one or more fatty substances which are liquid at ambient temperature, also known as oils, and which are compatible with one another. This fatty phase is macroscopically homogeneous.

The structuring of the liquid fatty phase makes it possible to limit its exudation from solid compositions and, furthermore, to limit, after deposition on the skin or lips, its migration over time into the wrinkles and fine lines, which is desired for a lipstick. The term "migration" is understood to mean overflowing of the composition and the color from the initial outline. Significant migration of the liquid fatty phase, laden with coloring materials, leads to an unsightly effect around the lips, particularly accentuating the wrinkles and fine lines. This migration is often mentioned by women as a major failing of conventional lipsticks.

This structuring can be obtained using solid particles or fillers. Furthermore, the fillers make it possible to reduce the sticky feel of some oils, such as castor oil or polyisobutenes, generally used in lipsticks.

Unfortunately, these particles or fillers have a tendency to render the composition matte, which is not always desirable in for example, a lipstick. This is because women are always looking for a lipstick in the stick form which deposits an ever glossier film.

The gloss is essentially related to the nature of the liquid fatty phase. Thus, it is possible to reduce the level of fillers in the composition in order to increase the gloss of a lipstick, but then the migration of the liquid fatty phase and/or the sticky feel of the composition increase. In other words, the level of fillers necessary for the preparation of a cosmetically acceptable stick is a brake on the gloss of the layer. Furthermore, the fillers have a tendency to dry out the skin and to register the cutaneous relief, such as the pores and wrinkles, thus accentuating local imperfections. This is contrary to the effect desired by women in, for example, a foundation, both for the human face and for the human body.

The Inventors have therefore envisaged the manufacture of a stick comprising little or nothing in the way of the types of fillers conventionally used in cosmetics. The fillers generally used in the cosmetic and dermatological fields are silicas, talcs, clays, kaolins, and polyamide (Nylon®) powders.

Waxes may be mentioned as another structuring agent used in the cosmetic or dermatological fields. The waxes used to date also have a tendency to render the composition matt because of their specific crystalline structure. Furthermore, they can confer a generally unpleasant feel to the composition.

One aspect of the invention is a composition for caring for and/or making up and/or treating keratinous substances, such as the skin and/or lips of the face and/or superficial body growths, which makes it possible to overcome at least one of these disadvantages.

Surprisingly, the Inventors have found that the use of specific polymers makes it possible to structure, even in the absence of conventional waxes and fillers, the liquid fatty phases in the form of a stick, the application of which to the lips results in a glossy and nonsticky film that has good coverage and decreased migration.

The invention applies not only to products for making up the lips but also to products for caring for and/or treating the skin, including the scalp, and the lips, such as daily care creams, lip balms and products for the antisun protection of the skin of the face or of the lips, to products for making up the skin, both of the human face and of the human body, such as foundations, such as when cast as a stick or in a dish, concealers, products for coloring the skin and temporary tattooing products, to body hygiene products, such as deodorants, for example stick deodorants, and to products for making up the eyes, such as eyeliners, for example eyeliners in the pencil form, and mascaras, such as mascaras in the cake form, or eyeshadows.

One aspect of the invention is a structured composition comprising at least one liquid fatty phase structured by at least one semi-crystalline -polymer having a low melting point and an organic structure, which is solid at ambient temperature and which has a melting temperature of less than 50° C., comprising a) a polymer backbone and b) at least one crystallizable organic side chain and/or one crystallizable organic block forming part of the said polymer backbone, the said polymer having a number-average molecular mass of greater than 2,000, with the liquid fatty phase and the polymer forming a physiologically acceptable medium.

One aspect of the invention is a composition comprising: at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, wherein said at least one semi-crystalline polymer has a number-average molecular mass of greater than 2,000, and wherein the liquid fatty phase and the at least one semi-crystalline polymer form a physiologically acceptable medium.

Another aspect of the invention is a lipstick comprising at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, wherein said at least one semi-crystalline polymer has a number-average molecular mass of greater than 2,000, and wherein the liquid fatty phase and the at least one semi-crystalline polymer form a physiologically acceptable medium for the lips.

Another aspect of the invention is a process for structuring, in the absence of wax and/or filler, a composition comprising a physiologically acceptable medium comprising at least one continuous liquid fatty phase, said process comprising including in said continuous liquid fatty phase an effective amount of at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, wherein said at least one semi-crystalline polymer has a number-average molecular mass of greater than 2,000, and wherein said composition is in solid form with a hardness ranging from 100 to 350 gf.

Another aspect of the invention is a processing for structuring, in the absence of wax and/or filler, a composition comprising a physiologically acceptable medium comprising at least one continuous liquid fatty phase, said process comprising including in said continuous liquid fatty phase a sufficient amount of at least one semi-crystalline polymer having an organic structure and a high melting point, wherein said semi-crystalline polymer is solid at ambient temperature, and has a melting temperature at least equal to 50° C., said at least one semi-crystalline polymer comprising i) a polymer backbone; and ii) at least one crystallizable organic side chain and/or at least one crystallizable organic block that forms part of the backbone of said at least one semi-crystalline polymer having a high melting point; wherein said at least one semi-crystalline polymer has a number-average molecular mass of greater than 2,000, and wherein said composition is in solid form and has a hardness ranging from 100 to 350 gf.

Yet another aspect of the invention is a process for structuring a composition comprising a physiologically acceptable medium comprising a liquid fatty phase, said process comprising including in said composition an effective amount of at least one semi-crystalline polymer having a low melting point and an organic structure, wherein said at least one semi-crystalline polymer is solid at ambient temperature and has a melting temperature of less than 50° C., and comprises a) a polymer backbone; and b) at least one crystallizable organic side chain and/or at least one crystallizable organic block that forms part of the backbone of said at least one semi-crystalline polymer with a low melting point, wherein said at least one semi-crystalline polymer has a number-average molecular mass of greater than 2,000, and wherein said liquid fatty phase is in solid form and is at least one of glossy, nonsticky, and covering.

Yet another aspect of the invention is a method of making a glossy and/or nonsticky and/or covering cosmetic composition comprising including in said composition at least one first semi-crystalline polymer having a low melting point and an organic structure, wherein said at least one first polymer is solid at ambient temperature, has a melting temperature of less than 50° C., and comprises a) a polymer backbone; and b) at least one crystallizable organic side chain and/or at least one crystallizable organic block that forms part of the backbone of said at least one first semi-crystalline polymer, wherein said at least one first semi-crystalline polymer has a number-average molecular mass of greater than 2,000, and at least one second semi-crystalline polymer having an organic structure and a high melting point, wherein said at least one second semi-crystalline polymer is solid at ambient temperature, has a melting temperature at least equal to 50° C., and comprises i) a polymer backbone; and ii) at least one crystallizable organic side chain and/or at least one crystallizable organic block that forms part of the backbone of said at least one second semi-crystalline polymer, wherein said at least one second semi-crystalline polymer has a number-average molecular mass of greater than 2,000.

Yet another aspect of the invention is a composition comprising: at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, wherein said at least one semi-crystalline polymer has a number-average molecular mass of greater than 2,000, and wherein the liquid fatty phase and the at least one semi-crystalline polymer form a physiologically acceptable medium; and wherein said semi-crystalline polymer does not comprise a polysaccharide backbone.

The composition of the invention can be provided in the form of a paste, solid or cream. It can be a simple oil-in-water, water-in-oil, or multiple emulsion, or a solid or soft anhydrous gel. It can be provided in the anhydrous form or in the form of an anhydrous gel, such as a stick or in a dish.

The term "polymers" is understood to mean, in accordance with the present invention, compounds comprising at least two repeat units, such as at least 3 repeat units and further such as at least 10 repeat units.

The term "semi-crystalline polymer" is understood to mean, in accordance with the present invention, polymers comprising a crystallizable part, a crystallizable pendent chain or a crystallizable block in the backbone, and an amorphous part in the backbone and exhibiting a first-order reversible phase change temperature, such as a melting temperature (solid-liquid transition). When the crystallizable part is in the form of a crystallizable block of the polymer backbone, the amorphous part of the polymer is in the form of an amorphous block; in this case, the semi-crystalline polymer is a block copolymer, for example of the diblock, triblock or multiblock type, comprising at least one crystallizable block and at least one amorphous block. The term "block" is understood to mean generally at least 5 identical repeat units. The crystallizable block or blocks are then different in chemical nature from the amorphous block or blocks.

The term "crystallizable chain" is understood to mean a chain comprising at least 6 carbon atoms.

U.S. Pat. No. 5,302,380 (DA) discloses cosmetic compositions for improved adhesion to the skin comprising atactic polypropylene homopolymers with a crystallinity of 0.1 to 15% and with a molecular weight of approximately 1,000 to 10,000. These polymers comprise neither a crystallizable pendent chain nor a crystallizable block. Their atactic arrangement, namely irregular arrangement, does not normally make crystallization possible. In addition, these polymers provide no discernible structuring of the compositions comprising them.

The composition according to the invention can additionally comprise at least one crystalline or semi-crystalline compound having an organic structure and having a high melting point, which is solid at ambient temperature and which has a melting temperature at least equal to 50° C. The terms "organic compound" or "having an organic structure" are understood to mean compounds comprising carbon atoms and hydrogen atoms and optionally heteroatoms, such as S, O, N, P, alone or in combination.

The semi-crystalline polymer or polymers having a melting temperature $F.p._2$ of less than 50° C. will be known as "polymers with a low melting point," and the crystalline or semi-crystalline compound or compounds having a melting temperature $F.p._1$ of greater than or equal to 50° C. will be known as "compounds with a high melting point". According to the invention, the melting point can be measured by any known method, such as with a differential scanning calorimeter (D.S.C.).

The structuring or gelling of the liquid fatty phase according to the invention is due to crystallization of the semi-crystalline polymer or polymers in the liquid fatty phase, in combination or not in combination with one or more crystalline compounds, and not to physical interaction of the dipole or hydrogen type between polymer chains, as disclosed in the U.S. Pat. No. 5,318,995 (D1) and EP-A-0 550 745 (D2). To obtain high thickening according to D1 and D2, it is necessary to form a highly interpenetrating crosslinked network by physical interactions between the chains of the polymers. This is obtained by using polymers with a number-average molecular mass of greater than 100,000. This high physical crosslinking of the polymer chains results in stiff and brittle gels which do not make possible the deposition of a film on keratinous substances and are difficult to take up with the finger. Furthermore, some of the polymers disclosed in these documents are insoluble or not very soluble in the oils conventionally used in cosmetics, which limits their use.

Suitable non-limiting examples of compounds having a high melting point, which can be used in the invention, include waxes with a high melting point, such as some polyethylene waxes, for example Epolene N-14, sold by Eastman Chemical Co.; carnauba waxes; and some microcrystalline waxes such as those sold by Tisco under the trade name "Tisco wax 88"; and semi-crystalline polymers with a high melting point. The semi-crystalline polymers having a high melting point can be semi-crystalline polymers with an organic structure which are solid at ambient temperature and can have a melting temperature of greater than or equal to 50° C., comprising a) an organic polymer backbone, and b) at least one crystallizable side organic chain and/or one crystallizable organic block forming part of the said polymer backbone, the said polymer having a number-average molecular mass of greater than 2,000.

For example, the compound with a high melting point is a second solid organic semi-crystalline polymer with a high melting point. However, it is possible to use, as compound with a high melting point, crystalline polymers which are solid at ambient temperature and which have a melting temperature of greater than 50° C., random polymers comprising controlled crystallization, as disclosed in EP-A-0 951 897 (D3) (the disclosure of which is incorporated by reference herein) and such as the commercial products Engage 8 401 and Engage 8 402 from Dupont de Nemours, with melting temperatures of 51° C. and 64° C. respectively, which are random ethylene/1-octene bipolymers.

The combination of one or more compounds with a high melting point, such as semi-crystalline polymers with a high melting point, with one or more polymers with a low melting point, makes it possible to confer on the composition good stability over time and with temperature. As defined herein, stability involves substantially avoiding, at room temperature, i.e., 25° C., exudation of oil.

Thus, it is possible to obtain a composition which remains macroscopically homogeneous without exudation of the liquid fatty phase, even in a moist atmosphere, for at least 2 months at 25° C. and atmospheric pressure.

Furthermore, the properties of nonmigration of the composition into the wrinkles and fine lines of the skin, such as around the lips, and also into the folds of the upper eyelid and around the eyes, are improved.

Semi-Crystalline Polymers with a High or Low Melting Point

For example, the semi-crystalline polymer or polymers (with a high or low melting point) of the composition of the invention comprise a number-average molecular mass $\overline{Mn}$ ranging from 2,000 to 800,000, such as from 3,000 to 500,000, for example from 4,000 to 150,000. According to another aspect of the invention, the number-average molecular mass is less than 100,000. as according to yet another aspect of the invention, the number-average molecular mass ranges from 4,000 to 99,000. In addition, they may exhibit a number-average molecular mass of greater than 5,600, for example ranging from 5,700 to 99,000.

The semi-crystalline polymer or polymers according to the invention acting as structuring agents are solids which are nondeformable at ambient temperature (25° C.) and atmospheric pressure (760 mm of Hg). They are capable of structuring, alone or as a mixture, the composition without addition of a specific surfactant nor a filler nor a wax.

According to the invention, the semi-crystalline polymers with a low melting point and/or the compounds with a high melting point are soluble in the fatty phase to at least 1% by weight at a temperature greater than their melting temperature. Apart from the crystallizable chains or blocks, the blocks of the polymers are amorphous. The term "crystallizable chain or block" is understood to mean, in accordance with the present invention, a chain or block which, if it were alone, would change reversibly from the amorphous state to the crystalline state, according to whether the temperature is above or below the melting temperature. A chain within the meaning of the invention is a group of atoms which is in the pendent or side position with respect to the backbone of the polymer. A block is a group of atoms belonging to the backbone, a group constituting one of the repeat units of the polymer.

The polymer backbone of the semi-crystalline polymers is soluble in the liquid fatty phase.

According to the invention, the semi-crystalline compound or compounds with a high melting point can be polymers having a melting temperature $M.p._1$ such that $50° C. \leq M.p._1 \leq 150° C.$, such as $55° C. \leq M.p._1 \leq 150° C.$ and further such as $60° C. \leq M.p._1 \leq 130° C.$ and the polymers with a low melting point may have a melting temperature $M.p._2$ such that $30° C. \leq M.p._2 < 50° C.$, such as $35° C. \leq M.p._2 \leq 45° C.$ This melting temperature is a first-order state change temperature.

Generally, the polymers with a low melting point exhibit a melting temperature $M.p._2$ at least equal to the temperature of the keratinous substrate which is to receive the composition according to the invention.

For example, the crystallizable block or chain or blocks or chains of the semi-crystalline polymers represent at least 30% of the total weight of each polymer such as at least 40%. The semi-crystalline polymers of the invention with crystallizable blocks are block or multiblock polymers. They can be obtained by polymerization of a monomer with reactive double (or ethylenic) bonds or by polycondensation. When the polymers of the invention are polymers with crystallizable side chains, the latter in the statistical or random form.

The semi-crystalline polymers of the invention can be synthetic in origin. In addition, they may not comprise a polysaccharide backbone. Generally, the crystallizable units (chains or blocks) of the semi-crystalline polymers according to the invention originate from monomer(s) with crystallizable block(s) or chain(s) used for the manufacture of semi-crystalline polymers.

According to the invention, the semi-crystalline polymer with a low melting point and the semi-crystalline polymer with a high melting point are chosen from block copolymers comprising at least one crystallizable block and at least one amorphous block, homopolymers and copolymers carrying at least one crystallizable side chain per repeat unit, and mixtures thereof.

The semi-crystalline polymers which can be used in the invention are:
- block copolymers of polyolefins with controlled crystallization, such as those for which the monomers are disclosed in EP-A-0 951 897;
- polycondensates of aliphatic or aromatic polyester type or aliphatic/aromatic copolyester type;
- homo- and copolymers carrying at least one crystallizable side chain and homo- or copolymers carrying, in the backbone, at least one crystallizable block, such as those disclosed in U.S. Pat. No. 5,156,911 (D4) (the disclosure of which is incorporated herein by reference);
- homo- and copolymers carrying at least one crystallizable side chain with fluorinated group(s), such as disclosed in document (D5,) WO-A-01/19333 (the disclosure of which is incorporated herein by reference); and
- mixtures thereof. In the last two cases, the crystallizable side chain or block or side chains or blocks are hydrophobic.

A) Semi-Crystalline Polymers with Crystallizable Side Chains

Mention may be made of those defined in U.S. Pat. No. 5,156,911 and WO-A-01/19333.

These are homopolymers or copolymers comprising from 50 to 100% by weight of units resulting from the polymerization of one or more monomers carrying a crystallizable hydrophobic side chain.

These homo- or copolymers can have any nature provided that they exhibit the conditions indicated below, with for example the characteristic of being soluble or dispersible in the liquid fatty phase by heating above their melting temperature M.p. They can result:
- from the polymerization, such as radical polymerization, of one or more monomers with double bond(s) or ethylenic monomers reactive with respect to polymerization, namely with a vinyl, (meth)acrylic or allyl group, and
- from the polycondensation of one or more monomers carrying coreactive groups (carboxylic or sulphonic acid, alcohol, amine or isocyanate groups), such as, for example, polyesters, polyurethanes, polyethers, polyureas or polyamides.

Generally, these polymers can be chosen from the homopolymers and copolymers resulting from the polymerization of at least one monomer with crystallizable chain(s) which can be represented by the formula X:

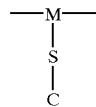

with M representing an atom of the polymer backbone, S representing a spacer, and C representing a crystallizable group.

The crystallizable chains "—S—C" can be aliphatic or aromatic and optimally fluorinated or perfluorinated. "S" can represent a linear or branched or cyclic $(CH_2)_n$ or $(CH_2CH_2O)_n$ or $(CH_2O)$ group with n an integer ranging from 0 to 22. For instance, "S" is a linear group. According to another aspect of the invention, "S" and "C" are different.

When the crystallizable chains "—S—C" are hydrocarbonaceous aliphatic chains, they comprise hydrocarbonaceous alkyl chains with at least 11 carbon atoms and at most 40 carbon atoms, such as most 24 carbon atoms. They can be aliphatic chains or alkyl chains having at least 12 carbon atoms; according to one aspect of the invention, they are $C_{14}$–$C_{24}$ alkyl chains. When they are fluorinated or perfluorinated alkyl chains, they comprise at least 6 fluorinated carbon atoms and can have at least 11 carbon atoms, at least 6 carbon atoms of which are fluorinated.

Mention may be made, as non-limiting examples of semi-crystalline polymers or copolymers with crystallizable chain(s), of those resulting from polymerization of one or more following monomers: saturated alkyl (meth)acrylates with the $C_{14}$–$C_{24}$ alkyl group; perfluoroalkyl (meth)acrylates with a $C_{11}$–$C_{15}$ perfluoroalkyl group; N-alkyl (meth)acrylamides with the $C_{14}$ to $C_{24}$ alkyl group, with or without a fluorine atom; vinyl esters with alkyl or perfluoro (alkyl) chains with the $C_{14}$ to $C_{24}$ alkyl group (with at least 6 fluorine atoms per one perfluoroalkyl chain); vinyl ethers with alkyl or perfluoro(alkyl) chains with the $C_{14}$ to $C_{24}$ alkyl group and at least 6 fluorine atoms per one perfluoroalkyl chain; $C_{14}$ to $C_{24}$ α-olefins such as, for example, octadecene; para-alkylstyrenes with an alkyl group comprising from 12 to 24 carbon atoms, and mixtures thereof.

When the polymers result from a polycondensation, the crystallizable hydrocarbonaceous and/or fluorinated chains as defined above are carried by a monomer which can be a diacid, a diol, a diamine or a diisocyanate.

When the polymers which are the subject-matter of the invention are copolymers, they additionally comprise from 0 to 50% of Y or Z groups resulting from the copolymerization:

α) of Y, which is a polar or nonpolar monomer or a mixture of the two:
  When Y is a polar monomer, it is a monomer carrying polyoxyalkylenated groups (for example oxyethylenated and/or oxypropylenated groups); a hydroxyalkyl (meth)acrylate, such as hydroxyethyl acrylate; (meth)acrylamide; an N-alkyl(meth)acrylamide; an N,N-dialkyl(meth)acrylamide, such as, for example, N,N-diisopropylacrylamide; N-vinylpyrrolidone (NVP); N-vinylcaprolactam; or a monomer carrying at least one carboxylic acid group, such as (meth)acrylic acid, crotonic acid, itaconic acid, maleic acid or fumaric acid, or carrying a carboxylic acid anhydride group, such as maleic anhydride, and mixtures thereof. When Y is a nonpolar monomer, it can be an ester of the linear, branched or cyclic alkyl (meth)acrylate type, a vinyl ester, an alkyl vinyl ether, an α-olefin, styrene or styrene substituted by a $C_1$–$C_{10}$ alkyl group, such as α-methylstyrene, or a macromonomer of the polyorganosiloxane type with vinyl unsaturation. The term "alkyl" is understood to mean, in accordance with the present invention, a saturated group, for example a $C_8$–$C_{24}$ group, unless specifically mentioned, and also a $C_{14}$–$C_{24}$ group.

β) of Z, which is a polar monomer or a mixture of polar monomers. In this case, Z has the same definition as the "polar Y" defined above.

For example, the semi-crystalline polymers with a crystallizable side chain are alkyl (meth)acrylate or alkyl(meth) acrylamide homopolymers with an alkyl group as defined above such as a $C_{14}$–$C_{24}$ alkyl group, copolymers of these monomers with a hydrophilic monomer can be different in nature from (meth)acrylic acid, such as N-vinylpyrrolidone or hydroxyethyl (meth)acrylate, and mixtures thereof.

B) Polymers Carrying, in the Backbone, at Least One Crystallizable Block

These are again polymers which are soluble or dispersible in the liquid fatty phase by heating above their melting point M.p. These polymers can be block copolymers composed of at least two blocks of different chemical natures, one of which is crystallizable.

Use may be made of the polymers defined in U.S. Pat. No. 5,156,911 (D4), (the disclosure of which is incorporated herein by reference), Block copolymers of olefin or of cycloolefin with a crystallizable chain, such as those resulting from the block polymerization of:
cyclobutene, cyclohexene, cyclooctene, norbornene (that is to say, bicyclo[2.2.1]hept-2-ene), 5-methylnorbornene, 5-ethylnorbornene, 5,6-dimethylnorbornene, 5,5,6-trimethyinorbornene, 5-ethylidenenorbornene, 5-phenylnorbornene, 5-benzylnorbornene, 5-vinyinorbornene, 1,4,5,8-dimethano-1,2,3,4,4a,5,8a-octahydronaphthalene, dicyclopentadiene or mixtures thereof,
with ethylene, propylene, 1-butene, 3-methyl-1-butene, 1-hexene, 4-methyl-1-pentene, 1-octene, 1-decene, 1-icosene or mixtures thereof,
and for example copoly(ethylene/norbornene) blocks and (ethylene/propylene/ethylidenenorbornene) terpolymer blocks. Use may also be made of those resulting from the block copolymerization of at least 2 $C_2$–$C_{16}$ α-olefins for example $C_2$–$C_{12}$ α-olefins, such as those mentioned above, and further such as the block bipolymers of ethylene and 1-octene.

The copolymers can be copolymers exhibiting at least one crystallizable block, the remainder of the copolymer being amorphous (at ambient temperature). These copolymers can, in addition, exhibit two crystallizable blocks of different chemical natures. Examples of copolymers are those which have, at ambient temperature, both a crystallizable block and a both hydrophobic and lipophilic amorphous block which are sequentially distributed; mention may be made, for example, of the polymers having one of the following crystallizable blocks and one of the following amorphous blocks:

Block crystallizable by nature: a) polyester, such as poly(alkylene terephthalate)s, b) polyolefin, such as polyethylenes or polypropylenes.

Amorphous and lipophilic block, such as: amorphous polyolefins or copoly(olefin)s, for example poly (isobutylene), hydrogenated polybutadiene or hydrogenated poly(isoprene).

Mention may be made, as suitable non-limiting examples of such copolymers with a crystallizable block and with an amorphous block, of:

α) poly(ε-caprolactone)-b-poly(butadiene) block copolymers, such as used hydrogenated, such as those described in the article D6, "Melting Behavior of poly(ε-caprolactone)-block-polybutadiene copolymers", by S. Nojima, Macromolecules, 32, 3727–3734 (1999) (the disclosure of which is incorporated by reference herein).

β) Block or multiblock hydrogenated poly(butylene terephthalate)-b-poly(isoprene) block copolymers, cited in the article D7, "Study of Morphological and Mechanical Properties of PP/PBT", by B. Boutevin et al., Polymer Bulletin, 34, 117–123 (1995) (the disclosure of which is incorporated by reference herein).

γ) The poly(ethylene)-b-copoly(ethylene/propylene) block copolymers cited in the articles D8, "Morphology of Semi-Crystalline Block Copolymers of ethylene-(ethylene-alt-propylene)", by P. Rangarajan et al., Macromolecules, 26, 4640–4645 (1993) and D9, "Polymer Aggregates with Crystalline Cores: the System poly (ethylene)-poly(ethylene-propylene)", P. Richter et al., Macromolecules, 30, 1053–1068 (1997) (the disclosures of which are incorporated by reference herein).

δ) The poly(ethylene)-b-poly(ethylethylene) block copolymers cited in the general article D10, "Crystallization in Block Copolymers", by I. W. Hamley, Advances in Polymer Science, vol. 148,113–137 (1999) (the disclosure of which is incorporated by reference herein).

The semi-crystalline polymers of the composition of the invention may or may not be partially crosslinked provided that the degree of crosslinking is not harmful to their dissolution or dispersion in the liquid fatty phase by heating above their melting temperature. The crosslinking can then be chemical crosslinking, by reaction with a multifunctional monomer during the polymerization. It can also be physical crosslinking, which can then be due either to the establishment of bonds of hydrogen or dipolar type between groups carried by the polymer, such as, for example, dipolar interactions between carboxylate ionomers, these interactions being low in degree and carried by the backbone of the polymer, or to phase separation between the crystallizable blocks and the amorphous blocks carried by the polymer.

The semi-crystalline polymers of the composition according to the invention can, for example, be not crosslinked.

According to an embodiment of the invention, the polymer can be chosen from the copolymers resulting from the polymerization of at least one monomer with a crystallizable chain, chosen from saturated $C_{14}$–$C_{24}$ alkyl (meth)acrylates; $C_{11}$–$C_{15}$ perfluoroalkyl (meth)acrylates; N-($C_{14}$ to $C_{24}$ alkyl)(meth)acrylamides, unsubstituted or substituted with at least one fluorine atom; vinyl esters with $C_{14}$ to $C_{24}$ alkyl or perfluoroalkyl chains; vinyl ethers with $C_{14}$ to $C_{24}$ alkyl or perfluoroalkyl chains; $C_{14}$ to $C_{24}$ α-olefins; or para-alkylstyrenes with an alkyl group comprising from 12 to 24 carbon atoms, with at least one optionally fluorinated $C_1$ to $C_{10}$ monocarboxylic acid ester or amide, which can be represented by the following formula:

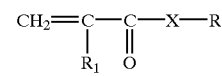

wherein $R_1$ is chosen from H and $CH_3$, R is chosen from optionally fluorinated $C_1$–$C_{10}$ alkyl groups, and X is chosen from O, NH and $NR_2$, where $R_2$ represents an optionally fluorinated $C_1$–$C_{10}$ alkyl group.

According to an embodiment of the invention, the polymer can result from a monomer with a crystallizable chain chosen from saturated $C_{14}$–$C_{22}$ alkyl (meth)acrylates.

Mention may be made, as non-limiting examples of structuring semi-crystalline polymers which can be used in the composition according to the invention, of the Intelimer® products from Landec described in the brochure D11 "Intelimer® polymers", Landec IP22 (Rev. 4–97) (the disclosure of which is incorporated herein by reference). These polymers are in the solid form at ambient temperature (25° C.). They carry crystallizable side chains and exhibit the above formula X.

i) The semicrystalline polymers with a low melting point can be, for example: those disclosed in examples 3, 4, 5, 7 and 9 of U.S. Pat. No. 5,156,911 comprising a —COOH group, resulting from the copolymerization of acrylic acid and of $C_5$ to $C_{16}$ alkyl (meth)acrylate with an M.p.$_2$ ranging from 20° C. to 35° C., such as from the copolymerization:

of acrylic acid, of hexadecyl acrylate and of isodecyl acrylate in a 1/16/3 ratio, of acrylic acid and of pentadecyl acrylate in a 1/19 ratio, of acrylic acid, of hexadecyl acrylate and of ethyl acrylate in a 2.5/76.5/20 ratio, of acrylic acid, of hexadecyl acrylate and of methyl acrylate in a 5/85/10 ratio, of acrylic acid and of polyoctadecyl methacrylate in a 2.5/97.5 ratio.

Use may also be made of the polymer Structure "O" from National Starch, such as that disclosed in U.S. Pat. No. 5,736,125 (the disclosure of which is incorporated by reference herein) with an M.p.$_2$ of 44° C., and of semi-crystalline polymers with crystallizable pendent chains comprising fluorinated groups, such as disclosed in Examples 1, 4, 6, 7 and 8 of the document (D5).

Use may also be made of the semi-crystalline polymers with a low melting point obtained by copolymerization of stearyl acrylate and of acrylic acid or of NVP as disclosed in U.S. Pat. No. 5,519,063 or D2 (EP-A-0 550 745) (the disclosures of which are incorporated by reference herein), such as those described in the polymer preparation Examples 1 and 2 below, with melting temperatures of 40° C. and 38° C. respectively.

ii) The semicrystalline polymers with a high melting point are, for example, the Intelimer described in document D11 with a melting temperature M.p.$_1$ of 56° C., which is a product which is viscous at ambient temperature, impermeable and nonsticky.

Use may also be made of the semi-crystalline polymers obtained by copolymerization of behenyl acrylate and of acrylic acid or of NVP as disclosed in the documents D13 and D2, and including those described in the polymer preparation Examples 3 and 4 below, with melting temperatures of 60° C. and 58° C. respectively.

For example, the semi-crystalline polymers with a low melting point and/or those with a high melting point do not comprise a carboxyl group.

The gelling of the fatty phase can be adjusted according to the nature of the polymers and their respective concentrations, and can be such that a rigid structure in the form of a stick is obtained.

The level of each polymer is chosen according to the desired hardness of the composition and according to the specific application envisaged. The respective amounts of polymer can be such that they make it possible to obtain a solid which can disintegrate, exhibiting a hardness ranging from 100 to 350 gf. This hardness can be measured by the "cheese wire" method, which comprises cutting a stick of lipstick with a diameter of 12.7 mm and in measuring the hardness at 20° C. by means of a DFGHS 2 dynamometer from Indelco-Chatillon moving at a rate of 100 mm/minute. It is expressed as the shear force (expressed in gram-force) needed to cut a stick under these conditions.

This hardness is such that the composition is self-supporting and can easily disintegrate to form a satisfactory layer on the skin and the lips. In addition, with this hardness, the composition of the invention in the cast form, such as a stick, possesses good impact strength.

For example, the composition of the invention is provided in the form of a solid stick with a hardness ranging from 100 gf to 350 gf, measured according to the "cheese wire" method. However, it is possible to use an amount of semi-crystalline polymer such that the composition is in the form of a soft paste which can be applied with a finger or using an applicator to keratinous substances.

In practice, the total amount of semi-crystalline polymer can represent from 0.1 to 80% of the total weight of the composition, such as from 0.5 to 40%, and further such as from 3 to 30%. For example, it represents more than 10% by weight of the composition.

According to one aspect of the invention, the compound with a high melting point (crystalline or semi-crystalline) and that with a low melting point can be in a ratio by weight ranging from 10/90 to 90/10, such as from 40/60 to 60/40.

For example, the ratio by weight of semi-crystalline polymer with an organic structure with respect to the liquid fatty phase may range from 0.20:1 to 0.60:1, for example from 0.25:1 to 0.50:1, to obtain a hard stick which disintegrates on contact with the skin or lips, such as with a hardness ranging from 100 to 350 gf.

The sticks according to the invention, when they are colored, make it possible, after application, to obtain a glossy and nonsticky layer which is homogeneous in color and which has good coverage (that is to say that the skin or lips do not appear under the make-up).

The Liquid Fatty Phase

The liquid fatty phase, structured by the semi-crystalline polymers with a low melting point and/or the semi-crystalline polymers with a high melting point, constitutes the continuous phase of the composition. This fatty phase can comprise one or more nonpolar or polar oils, or a mixture of nonpolar oil(s) and of polar oil(s).

The nonpolar oils according to the invention can be silicone oils, such as linear or cyclic polydimethylsiloxanes (PDMSs) which are liquid at ambient temperature; polydimethylsiloxanes comprising pendent alkyl, alkoxy or phenyl groups and/or alkyl, alkoxy or phenyl groups at the end of the silicone chain, which groups have from 2 to 24 carbon atoms and which polydimethylsiloxanes are liquid at ambient temperature; liquid phenylated silicones, such as phenyl trimethicones, phenyl dimethicones, phenyltrimethylsiloxydiphenylsiloxanes, diphenyl dimethicones, diphenylmethyidiphenyltrisiloxanes or (2-phenylethyl) trimethylsiloxysilicates; liquid linear or branched hydrocarbons or fluorocarbons of synthetic or mineral origin, such as liquid paraffins and their derivatives, liquid petrolatum, polydecenes, hydrogenated polyisobutene, such as Parleam® sold by Nippon Oil Fats, or squalane; or mixtures thereof. For example, the nonpolar oils that may be used include liquid nonpolar oils of the hydrocarbonaceous type of mineral or synthetic origin, and can be chosen from Parleam® oil (hydrogenated isoparaffin), isoparaffins, squalene and mixtures thereof. According to one aspect of the invention, the liquid fatty phase comprises at least one hydrocarbonaceous oil of mineral or synthetic origin.

The term "hydrocarbonaceous oil" is understood to mean, within the meaning of the invention, oils predominantly comprising carbon atoms and hydrogen atoms such as alkyl or alkenyl chains, such as alkanes or alkenes, but also oils with an alkyl or alkenyl chain comprising one or more ether, ester, hydroxyl or carboxylic acid groups.

It is possible to add polar oils to the nonpolar oils, the nonpolar oils can act as cosolvent for the polar oils.

For example, the polar oils of the invention are:

hydrocarbonaceous vegetable oils with a high content of triglycerides composed of esters of ($C_8$ to $C_{24}$) fatty acids and of glycerol, the fatty acids of which can have various chain lengths, it being possible for the chains to be linear or branched and saturated or unsaturated; these oils can be wheat germ, maize, sunflower, karite, castor, sweet almond, macadamia, apricot, soybean, rapeseed, cottonseed, alfalfa, poppy, pumpkinseed, sesame, cucumber, avocado, hazelnut, grape seed, blackcurrant seed, evening primrose, millet, barley, quinoa, olive, rye, safflower, candlenut, passionflower or musk rose oils; or triglycerides of caprylic/capric acids, such as those sold by Stearineries Dubois or those sold under the names Miglyol 810, 812 and 818 by Dynamit Nobel;

synthetic oils of formula $R_5COOR_6$ in which $R_5$ is chosen from residues of linear and branched higher fatty acids comprising from 7 to 40 carbon atoms and $R_6$ is chosen from branched hydrocarbonaceous chains comprising from 3 to 40 carbon atoms, such as, for example purcellin oil (cetearyl octanoate), isononyl isononanoate or $C_{12}$ to $C_{15}$ alkyl benzoate;

synthetic esters and ethers, such as isopropyl myristate, 2-ethylhexyl palmitate, octanoates, decanoates or ricinoleates of alcohols or of polyalcohols, hydroxylated esters, such as isostearyl lactate or diisostearyl malate; and pentaerythritol esters;

$C_8$ to $C_{26}$ fatty alcohols, such as oleyl alcohol;

fatty acids having from 12 to 22 carbon atoms, such as oleic acid, linoleic acid and linolenic acid;

mixtures thereof.

According to one aspect of the invention, the fatty phase represents, for example, an amount ranging from 5 to 99% of the total weight of the composition, such as from 20 to 80%. It may represent at least 60% of the total weight of the composition.

The Additives

The composition of the invention can additionally comprise any additive conventionally used in the field under consideration chosen from water, optionally thickened by an aqueous-phase thickener or gelling agent, coloring materials, antioxidants, essential oils, preservatives, fragrances, fillers, dispersing agents, pasty fatty substances or waxes other than the compounds with a high melting point, neutralizing agents, and mixtures thereof. These additives can be present in the composition according to the amounts generally used in the cosmetics and dermatological field, such as in an amount ranging from 0.01 to 50% of the total weight of the composition and further such as of 0.1 to 20%. The water can represent up to 70% of the total weight of the composition.

Of course, a person skilled in the art would take care to choose the optional additional additives and/or their amounts so that the advantageous properties of the composition according to the invention, namely gloss, nonstickiness, coverage and nonmigration, are not, or not substantially, detrimentally affected by the envisaged addition.

The composition according to the invention can be provided in the form of a dermatological composition or of a composition for caring for the skin and/or superficial body growths, or in the form of a sun protection composition, care composition for the face or body, or body hygiene composition, such as in the form of a deodorant. It can then be provided in the colorless form. It can then be used as care base for the skin, superficial body growths or lips (lip balms, protecting the lips from the cold and/or the sun and/or the wind, care cream for the skin, nails or hair), a shampoo or a conditioner, or a sun protection product.

The composition of the invention can also be provided in the form of a colored product, such as for making up the skin, optionally exhibiting care or treatment properties, and can be a foundation, a blusher, a face powder, an eyeshadow, a concealer, an eyeliner or a product for making up the body; for making up the lips, such as a lipstick, a lip gloss or a lip pencil, optionally exhibiting care or treatment properties; or for making up the superficial body growths, such as the nails, eyelashes (in the form of a mascara), eyebrows and hair.

Of course, the composition of the invention has to be cosmetically or dermatologically acceptable, namely comprising a nontoxic physiologically acceptable medium capable of being applied to the skin, superficial body growths or lips of the face of human beings. The term "cosmetically acceptable" is understood to mean, in accordance with the invention, a composition with at least one of a pleasant appearance, pleasant smell, pleasant feel, and pleasant taste.

The composition may comprise a coloring material which can be chosen from lipophilic dyes, hydrophilic dyes, pigments and pearlescent agents commonly used in cosmetic or dermatological compositions, and mixtures thereof. This coloring material is generally present in an amount ranging from 0.01 to 50% (on a dry basis) of the total weight of the composition, such as of 5 to 30% (if present). The terms "pigments" and "pearlescent agents" are understood to mean particles which are solid and insoluble at ambient temperature in the physiologically acceptable medium of the composition.

The fat-soluble dyes are, for example, Sudan red, D & C Red 17, D & C Green 6, β-carotene, soybean oil, Sudan brown, D & C Yellow 11, D & C Violet 2, D & C orange 5, quinoline yellow or annatto. They can represent from 0 to 20% of the weight of the composition, for example from 0.01 to 6%. The water-soluble dyes can be, for example, beetroot juice or methylene blue, and can represent up to 6% of the total weight of the composition.

The pigments can be white or colored, inorganic and/or organic, spherical or nonspherical, lamellar or nonlamellar and coated or uncoated. Mention may be made, among inorganic pigments, of titanium dioxide or zinc dioxide, optionally treated at the surface, zirconium or cerium oxides, iron or chromium oxides, manganese violet, ultramarine blue, chromium hydrate and ferric blue. Mention may be made, among organic pigments, of carbon black, pigments of D & C type, and lakes based on cochineal carmine or on barium, strontium, calcium or aluminium (such as D & C red 27, 21 or 7, D & C yellow 5 or 6, or F D & C blue No. 1). The pigments can represent from 0 to 40% (0.01 to 40%), such as from 0.5 to 35% and further such as from 2 to 25% of the total weight of the composition (if present).

The pearlescent pigments (or pearlescent agents) can be chosen from white pearlescent pigments, such as mica covered with titanium oxide or with bismuth oxychloride, colored pearlescent pigments, such as titanium oxide-coated mica with iron oxides, titanium oxide-coated mica with ferric blue or chromium oxide, or titanium oxide-coated mica with an organic pigment of the abovementioned type, and pearlescent pigments based on bismuth oxychloride or interferential pigments, such as liquid crystal or multilayer pigments. They can represent from 0 to 25% (0.05 to 25%) of the total weight of the composition such as from 0.1 to 15% (if present).

For example, the coloring material comprises pigments or pearlescent agents.

For example, the pigments and pearlescent agents can be introduced into the composition in the form of a pigmentary paste.

The term "pigmentary paste" is understood to mean, within the meaning of the invention, a concentrated colloidal dispersion of particles in a continuous medium, which particles are solid at ambient temperature, are colored and are coated or uncoated and which dispersion is stabilized at the surface using a dispersing agent or optionally without a dispersing agent.

The dispersing agent serves to protect the dispersed particles against their agglomeration or flocculation. The concentration of dispersing agent generally used to stabilize solid particles in dispersion for instance a colloidal dispersion is from 0.3 to 5 mg/m$^2$ of particle surface area, such as from 0.5 to 4 mg/m$^2$ of particle surface area. This dispersing agent can be a surfactant, an oligomer, a polymer or a mixture of several of them, carrying one or more functionalities having a high affinity for the surface of the particles to be dispersed. It can attach physically or chemically to the surface of the particles to be dispersed. In addition, it exhibits at least one functional group compatible with or soluble in the continuous medium. For example, use is made of esters of poly(12-hydroxystearic) acid, such as the stearate of poly(12-hydroxystearic) acid, for example that sold under the name of Solsperse 21 000 by Avecia, polyglyceryl-2 dipolyhydroxystearate (CTFA name), sold under the reference Dehymuls PGPH by Henkel, poly(12-hydroxystearic) acid, sold under the reference Arlacel P100 by Uniqema, and mixtures thereof. These dispersing agents can, in addition, be used as additive without, however, forming part of a particulate or pigmentary paste.

The colloidal dispersion is a suspension of particles of generally micronic size (<10 $\mu$m) in a continuous medium. The fraction by volume of particles in a concentrated dispersion is from 20% to 40%, such as greater than 30%.

The particles dispersed in the medium can be composed of inorganic or organic particles or of their mixtures, such as those described above.

The continuous medium of the pigmentary paste can have any composition and can comprise any solvent or liquid fatty substance and mixtures thereof. For example, the liquid medium of the pigmentary paste can be one of the oils which it is desired to use in the composition.

Use may also be made, in the composition of the invention, of at least one wax, such as those used up to the present time in cosmetics.

A wax, in accordance with the invention, is a lipophilic fatty compound which is solid at ambient temperature (25° C.) and atmospheric pressure (760 mmHg), which has a reversible solid/liquid state change, which has a melting temperature of greater than 40° C. such as greater than 50° C. which can range up to 200° C., and which exhibits, in the solid state, an anisotropic crystalline organization. The size of the crystals is such that the crystals diffract and/or scatter light, conferring a more or less opaque cloudy appearance on the composition. On bringing the wax to its melting temperature, it is possible to render it miscible with the oils and to form a microscopically homogeneous mixture but, on returning the temperature of the mixture to ambient temperature, recrystallization of the wax in the oils of the mixture is obtained. This recrystallization from the mixture may be responsible for the decrease in the gloss of the said mixture. Consequently, the composition can comprise little or nothing in the way of conventional waxes and less than 10% by weight of conventional wax such as less than 5% with respect to the total weight of the composition.

Conventional waxes, in accordance with the present invention, are those generally used in the cosmetics and dermatological fields; they can be of natural origin, such as beeswax, candelilla wax, ouricury wax, Japan wax, cork fibre wax or sugarcane wax, paraffin or lignite waxes, microcrystalline waxes with a melting point greater than 50° C., lanolin wax, montan wax, ozokerites, or hydrogenated oils, such as hydrogenated jojoba oil, but can also be of synthetic origin, such as polyethylene waxes resulting from the polymerization of ethylene and the waxes obtained by the Fischer-Tropsch synthesis with a melting point greater than 50° C., fatty acid esters and glycerides which are solid at 50° C., or silicone waxes, such as alkyl or alkoxy poly(di)methylsiloxanes and/or poly(di)methylsiloxane esters which are solid at 50° C.

For instance the composition of the invention can comprise little or nothing in the way of "mattifying" fillers such as less than 5% of mattifying filler. This may be the case when it is desired to obtain a glossy layer on keratinous substances, such as the lips, eyelashes and hair. For a foundation, on the other hand, fillers of this type may be used. A mattifying filler is generally a filler which absorbs sweat and/or sebum from the skin, such as silicas, talcs, clays, kaolins, polyamide (Nylon®) powders or starch.

The composition according to the invention can be manufactured by known processes used generally in the cosmetics or dermatological field. It can be manufactured by the process which comprises heating the polymer at least to its melting temperature, in adding thereto the optional amphiphilic compound or compounds, the coloring materials soluble in the medium, the pigmentary pastes and the additives, and in then mixing the combined mixture until a clear and translucent solution is obtained. The homogeneous mixture obtained can then be poured into an appropriate mould, such as a lipstick mould, or directly into the packaging articles for example, case or dish.

For instance, the composition of the invention can be a lipstick comprising at least one liquid fatty phase structured by at least one semi-crystalline polymer with a low melting point, with an organic structure, which is solid at ambient temperature and which has a melting temperature of less than 50° C., comprising a) a polymer backbone and b) at least one crystallizable organic side chain and/or one crystallizable organic block forming part of the polymer backbone of the polymer with a low melting point, the said polymer having a number-average molecular mass of greater than 2,000, the liquid fatty phase and the polymer forming a medium which is physiologically acceptable for the lips. For example, this lipstick can comprise a continuous fatty phase composed of all or a portion of the structured liquid fatty phase. For example, this lipstick can comprise a compound with a high melting point as described above, such as a second semi-crystalline polymer.

A further aspect of the invention is a cosmetic process for caring for, making up or treating the keratinous substances of human beings and in particular the skin or the lips of the face and the superficial body growths of human beings, comprising the application, to the keratinous substances, of the composition, such as cosmetic composition, as defined above.

Yet another aspect of the invention is the cosmetic use of a sufficient amount of at least one semi-crystalline polymer with a low melting point, with an organic structure, which is solid at ambient temperature and which has a melting temperature of less than 50° C., comprising a) a polymer backbone and b) at least one crystallizable organic side chain and/or one crystallizable organic block forming part of the polymer backbone of the polymer with a low melting point, the said polymer having a number-average molecular mass of greater than 2,000, in a composition, such as a cosmetic composition, comprising a physiologically acceptable medium comprising at least one continuous liquid fatty phase, as agent for structuring, in the absence of wax and/or filler, the continuous liquid fatty phase in the form of a solid with a hardness ranging from 100 to 350 gf. It is possible, according to the invention, to combine, with this polymer with a low melting point, a crystalline or semi-crystalline compound with an organic structure which is solid at ambient temperature and which has a melting temperature of at least 50° C., such as, for example, those selected above.

A further aspect of the invention is the use, such as cosmetic use, of a sufficient amount of at least one semi-crystalline polymer with an organic structure and with a high melting point, which is solid at ambient temperature and which has a melting temperature at least equal to 50° C., comprising i) a polymer backbone and ii) at least one crystallizable organic side chain and/or one crystallizable organic block forming part of the backbone of the polymer with a high melting point, the said polymer having a number-average molecular mass of greater than 2,000, in a composition, such as a cosmetic composition, comprising a continuous liquid fatty phase, as agent for structuring, in the absence of wax and/or filler, the continuous liquid fatty phase in the form of a solid with a hardness ranging from 100 to 350 gf. It is possible, according to the invention, to combine, with this polymer with a high melting point, a crystalline or semi-crystalline compound with an organic structure which is solid at ambient temperature and which has a melting temperature of less than 50° C., such as, for example, those cited above.

A further aspect of the invention is the cosmetic use of a sufficient amount of at least one semi-crystalline polymer with an organic structure and with a low melting point, which is solid at ambient temperature and which has a melting temperature of less than 50° C., comprising a) a polymer backbone and b) at least one crystallizable organic side chain and/or one crystallizable organic block forming part of the polymer with a low melting point, the said polymer having a number-average molecular mass of greater than 2,000, in a composition, such as a cosmetic composition, comprising a physiologically acceptable medium and comprising a liquid fatty phase, for structuring the liquid fatty phase in the form of a glossy and/or non-sticky and/or covering solid.

A further aspect of the invention is the use, such as cosmetic use, of the combination of a first semi-crystalline polymer with a low melting point and with an organic structure, which is solid at ambient temperature and which has a melting temperature of less than 50° C., comprising a) a polymer backbone and b) at least one crystallizable organic side chain and/or one crystallizable organic block forming part of the first polymer, the said first polymer having a number-average molecular mass of greater than 2,000, with a second semi-crystalline polymer with an organic structure and with a high melting point, which is solid at ambient temperature and which has a melting temperature at least equal to 50° C., comprising i) a polymer backbone and ii) at least one crystallizable organic side chain and/or one crystallizable organic block forming part of the backbone of the second polymer, the said second polymer having a number-average molecular mass of greater than 2,000, in a composition, such as a cosmetic composition, comprising a physiologically acceptable medium that is glossy and/or nonmigrating and/or nonsticky and/or covering. For instance, the composition is in the form of a glossy and/or nonsticky and/or covering solid. It is possible to replace all or a portion of this second polymer with any other compound with a high melting point as described above.

The cosmetic composition according to the invention may exhibit treating properties. For example, the combination of the polymer with a low melting point and of the polymer with a high melting point can be used for the manufacture of a physiologically acceptable composition such as a nonmigrating dermatological composition. Thus, it can be possible to keep the composition in place there where it has been deposited and to thus improve its local action and its effectiveness.

The invention is illustrated in more detail in the following examples. The amounts are given as percentages by mass.

I) EXAMPLES OF THE MANUFACTURE OF SEMI-CRYSTALLINE POLYMERS

Example 1

Acidic Polymer with a Melting Point of 40° C.

120 g of Parleam are introduced into a 1 l reactor equipped with a central anchor stirrer, a reflux condenser and thermometer and are heated from ambient temperature to 80° C. for 45 min. The following mixture $C_1$:
40 g of cyclohexane +4 g of Triganox 141 [2,5-bis(2-ethylhexanoylperoxy)-2,5-dimethylhexane],
is introduced at 80° C. over 2 h.
30 min after beginning to run in the mixture $C_1$, the mixture $C_2$, composed of:
190 g of stearyl acrylate +10 g of acrylic acid +400 g of cyclohexane, is introduced over 1 h 30.
At the end of the two additions, the reaction mixture is allowed to act for an additional 3 h at 80° C. and then all the cyclohexane present in the reaction mixture is distilled off at atmospheric pressure.
The polymer comprising 60% by weight of active material in Parleam is then obtained. Its weight-average molecular mass $M_w$ is 35,000, expressed as polystyrene equivalent, and its melting temperature M.t. is 40° C.±1° C., measured by D.S.C.

Example 2

Basic Polymer with a Melting Point of 38° C.

The same procedure is applied as in Example 1, except that N-vinylpyrrolidone is used instead of acrylic acid.
The polymer obtained is at 60% by weight of active material in Parleam, its weight-average molecular mass $M_w$ is 38 000 and its M.t. is 38° C.

Example 3

Acidic Polymer with a Melting Point of 60° C.

The same procedure is applied as in Example 1, except that behenyl acrylate is used instead of stearyl acrylate. The polymer obtained is at 60% by weight of active material in Parleam. Its weight-average molecular mass $M_w$ is 42 000 and its M.t. is 60° C.

Example 4

Basic Polymer with a Melting Point of 58° C.

The same procedure is applied as in Example 2, except that behenyl acrylate is used instead of stearyl acrylate. The polymer obtained is at 60% by weight of active material in Parleam®. Its $M_w$ is 45 000 and its M.t. is 58° C.

II) COMPOSITION EXAMPLES

Example 5

Lipstick Formula

| | |
|---|---|
| 95/5 Stearyl acrylate/NVP copolymer comprising 60% of active material in Parleam according to Example 2 | 10.1% |
| Behenyl acrylate/acrylic acid copolymer comprising 60% of active material in Parleam according to Example 3 | 10.1% |
| Pigmentary paste | 17.7% |
| Hydrogenated isoparaffin (Parleam) | q.s. for 100% |

Preparation: The polymers are dissolved in a portion of the oil at 100° C. and then the addition is carried out of the pigments, milled beforehand using a triple roll mill, with a portion of the oily phase. The entire combination is mixed using a magnetic bar and then poured into lipstick moulds. The pigmentary paste contains 49% of pigments (D & C Red No. 7+Yellow No. 6 (aluminium lake)+titanium dioxide), 7.5% of poly(12-hydroxystearic) acid stearate and 43.5% of Parleam, which is a hydrogenated isoparaffin (6–8 mol of isobutylene).

The pigmentary paste is obtained using a disperser-mill of Dispermat type and heating the Parleam at 25–30° C. for approximately 30 minutes. It is stable for at least 3 months at ambient temperature, that is to say that no sedimentation is observable even with stirring.

A stick of lipstick is obtained which has a hardness of 117 gf, measured by the "cheese wire" method. The lipstick obtained is glossy, nonsticky and nonmigrating. This was confirmed by a comparative sensory test, by half-lips, with a glossy product of the prior art Rouge Absolu from Lancôme. The lipstick of the invention was judged to be as glossy on application as that of the prior art by all the testers, with much slighter migration.

Example 6

Lipstick Formula

| | |
|---|---|
| Copolymer according to Example 3 | 12.5% |
| Copolymer according to Example 1 | 12.5% |
| Pigmentary paste | 17.7% |
| Hydrogenated isoparaffin | q.s. for 100% |

The composition of the pigmentary paste is identical to that of Example 5.

This lipstick in the form of a stick was prepared as in Example 5. It is glossy, nonsticky and nonmigrating. It was judged by a panel of experts in comparison with a lipstick of the prior art Rouge Magnétique from Lancôme, regarded as not very migrating. The lipstick of the invention was judged to be glossier than Rouge Magnétique for comparable properties of nonmigration.

The lipsticks of the prior art, Rouge Absolu and Rouge Magnétique, do not comprise semi-crystalline polymers with a low melting point, in combination with a crystalline or semi-crystalline compound with a high melting point.

Example 7

Lipstick Formula

It differs from Example 5 by the use of a polyethylene wax (Performalen 500, sold by Petrolite), with a melting point of 83° C. to within about 1° C., instead of the polymer of Example 3. The cosmetic properties obtained are comparable to those of the formula of Example 5.

Example 8

Lipstick Formula

| | |
|---|---|
| Engage 8400 | 10.0% |
| Copolymer of Example 1 | 10.1% |
| Pigmentary paste | 17.7% |
| Hydrogenated liquid paraffin | q.s. for 100% |

The pigmentary paste is identical to that of Example 5. The manufacture of this lipstick as a stick is identical to that of Example 5.

Example 9

Lipstick Formula

| | |
|---|---|
| Stearyl acrylate/acrylic acid (95/5) copolymer comprising 50% of active material in Parleam | 25% |
| Behenyl acrylate/N-vinylpyrrolidone (95/5) copolymer comprising 62.5% of active material in Parleam | 25% |
| Solsperse 21000 (poly(12-hydroxystearic) acid) | 2% |
| Pigments | 8.66% |
| Hydrogenated isoparaffin | q.s. for 100% |

Preparation: the polymers are dissolved in a portion of the oil at 100° C. and then the addition is carried out of the pigments, which were milled beforehand using a triple roll mill, with a portion of the oily phase. The entire combination is mixed using a magnetic bar and is then poured into lipstick moulds. The pigments are in accordance with Example 5.

A stick of lipstick is obtained which has a hardness of 227 gf, measured by the "cheese wire" method, is nonmigrating, is nonsticky, is easily deposited on the lips and gives a satiny layer.

Example 10

Lipstick Formula

| | |
|---|---|
| Behenyl methacrylate/acrylic acid (95/5) copolymer at 50% in Parleam | 25% |
| Behenyl acrylate/N-vinylpyrrolidone (95/5) copolymer at 62.5% in Parleam | 25% |
| Solsperse 21000 (poly(12-hydroxystearic) acid) | 2% |
| Pigments | 8.66% |
| Hydrogenated isoparaffin | q.s. for 100% |

Preparation: the polymers are dissolved in a portion of the oil at 100° C. and then the addition is carried out of the pigments, which were milled beforehand using a triple roll mill, with a portion of the oily phase. The entire combination is mixed using a magnetic bar and is then poured into lipstick moulds. The pigments are in accordance with Example 5.

A stick of lipstick is obtained which has a hardness of 342 gf, measured by the "cheese wire" method, is nonmigrating, is nonsticky, is easily deposited on the lips, and gives a satiny layer.

What is claimed is:

1. A composition comprising:
   at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, and
   at least one compound chosen from crystalline and semi-crystalline compounds having an organic structure and a high melting point, wherein said compound is solid at ambient temperature and has a melting temperature of at least equal to 50° C.
      wherein said at least one semi-crystalline polymer has a number-average molecular mass of greater than 2,000, and wherein the liquid fatty phase and the at least one semi-crystalline polymer form a physiologically acceptable medium.

2. The composition of claim 1, wherein the at least one compound is chosen from second polymers, wherein each of said second polymers has a high melting point and comprises i) a polymer backbone, and ii) at least one crystallizable organic side chain and/or one crystallizable organic block forming part of the backbone of the said second polymer, and further wherein each of said second polymers has a number-average molecular mass of greater than 2,000.

3. The composition of claim 2, wherein said at least one semi-crystalline polymer and/or said second polymers have a number-average molecular mass ranging from 3,000 to 500,000.

4. The composition of claim 3, wherein said at least one semi-crystalline polymer and/or said second polymers have a number-average molecular mass ranging from 4,000 to 99,000.

5. The composition of claim 1, wherein said at least one semi-crystalline polymer and/or said at least one compound is soluble in the liquid fatty phase at a temperature greater than their melting temperatures.

6. The composition of claim 1, wherein said at least one semi-crystalline polymer has a melting temperature, M.p.$_2$, ranging from greater than or equal to 30° C. to less than 50° C.

7. The composition of claim 1, wherein said at least one compound has a melting temperature, M.p.$_1$, ranging from greater than or equal to 55° C. to less than or equal to 150° C.

8. The composition of claim 7, wherein said at least one compound has a melting temperature, M.p.$_1$, ranging from greater than or equal to 60° C. to less than or equal to 130° C.

9. The composition of claim 2, wherein said at least one semi-crystalline polymer and/or said second polymers are chosen from block copolymers comprising at least one crystallizable block and at least one amorphous block, and from homopolymers and copolymers comprising at least one crystallizable side chain per repeat unit.

10. The composition of claim 9, wherein in said block copolymers there are at least two crystallizable blocks that are not identical and/or there are at least two amorphous blocks that are not identical.

11. The composition of claim 2, wherein said at least one semi-crystalline polymer and/or said second polymers are chosen from:
   block copolymers of polyolefins with controlled crystallization;
   aliphatic and aromatic polyester polycondensates and aliphatic/aromatic copolyesters; and
   homo- and copolymers carrying at least one crystallizable side chain.

12. The composition of claim 2, wherein said at least one semi-crystalline polymer and/or said second polymers are chosen from homopolymers and copolymers comprising from 50% to 100% by weight of units resulting from polymerization of at least one monomer carrying at least one crystallizable hydrophobic side chain.

13. The composition of claim 2, wherein said at least one semi-crystalline polymer and/or said second polymers are chosen from homopolymers and copolymers resulting from the polymerization of at least one monomer having at least one crystallizable chain of formula X:

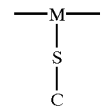

wherein M represents an atom of the polymer backbone,
S represents a spacer, C represents a crystallizable group, and "S—C" represents an alkyl chain optionally chosen from optionally fluorinated and perfluorinated alkyl chains.

14. The composition of claim 13, wherein said at least one semi-crystalline polymer and/or said second polymers are chosen from homopolymers and copolymers resulting from the polymerization of at least one monomer having at least one crystallizable chain of formula X:

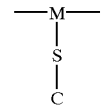

wherein "S—C" are chosen from fluorinated and perfluorinated alkyl chains having at least 11 carbon atoms.

15. The composition of claim 2, wherein said at least one semi-crystalline polymer and/or said second polymers are chosen from polymers resulting from polymerization of at least one monomer chosen from acrylic acid, methacrylic acid, crotonic acid, itaconic acid, maleic acid, and maleic anhydride.

16. The composition of claim 2, wherein said at least one semi-crystalline polymer and/or said second polymers are chosen from homopolymers and copolymers resulting from polymerization of at least one monomer having at least one crystallizable chain chosen from saturated $C_{14}$–$C_{24}$ alkyl (meth)acrylates; $C_{11}$–$C_{15}$ perfluoroalkyl (meth)acrylates; N-($C_{14}$ to $C_{24}$ alkyl)(meth)acrylamides unsubstituted or substituted with at least one fluorine atom; vinyl esters with alkyl chains chosen from $C_{14}$ to $C_{24}$ alkyl chains and $C_{14}$ to $C_{24}$ perfluoroalkyl chains; vinyl ethers with alkyl chains chosen from $C_{14}$ to $C_{24}$ alkyl chains and $C_{14}$ to $C_{24}$ perfluoroalkyl chains; $C_{14}$ to $C_{24}$ α-olefins; and para-alkylstyrenes wherein said alkyl is chosen from alkyl groups comprising from 12 to 24 carbon atoms.

17. The composition of claim 2, wherein said at least one semi-crystalline polymer and/or said second polymers are chosen from copolymers resulting from the polymerization of at least one monomer having at least one crystallizable chain, wherein said at least one crystallizable chain is chosen from saturated $C_{14}$–$C_{24}$ alkyl (meth)acrylates; $C_{11}$–$C_{15}$ perfluoroalkyl (meth)acrylates; N-($C_{14}$ to $C_{24}$alkyl)(meth) acrylamides unsubstituted or substituted with at least one fluorine atom; vinyl esters with alkyl chains chosen from $C_{14}$ to $C_{24}$ alkyl chains and $C_{14}$ to $C_{24}$perfluoroalkyl chains; vinyl ethers with alkyl chains chosen from $C_{14}$ to $C_{24}$ alkyl chains and $C_{14}$ to $C_{24}$ perfluoroalkyl chains; $C_{14}$ to $C_{24}$ α-olefins, and para-alkylstyrenes, wherein said alkyl is chosen from alkyl groups comprising from 12 to 24 carbon atoms, with at least one optionally fluorinated monomer chosen from $C_1$ to $C_{10}$ monocarboxylic acid esters and amides.

18. The composition of claim 2, wherein said at least one semi-crystalline polymer and/or said second polymers are chosen from homopolymers of alkyl (meth)acrylate, wherein said alkyl group is chosen from $C_{14}$ to $C_{24}$ alkyl groups, homopolymers of alkyl(meth)acrylamide, wherein said alkyl group is chosen from $C_{14}$ to $C_{24}$ alkyl groups, and copolymers of at least one monomer chosen from alkyl (meth)acrylate, wherein said alkyl group is chosen from $C_{14}$ to $C_{24}$ alkyl groups, and alkyl(meth)acrylamide, wherein said alkyl group is chosen from $C_{14}$ to $C_{24}$ alkyl groups, with at least one hydrophilic monomer.

19. The composition of claim 2, wherein said at least one semi-crystalline polymer and/or said second polymers result from a monomer having at least one crystallizable chain chosen from saturated $C_{14}$ to $C_{22}$ alkyl (meth)acrylates.

20. The composition of claim 2, wherein the at least one crystallizable organic side chain and/or the at least one crystallizable block of said at least one semi-crystalline polymer and/or said second polymers represent at least 30% of the total weight of each polymer.

21. The composition of claim 1, wherein said at least one semi-crystalline polymer and/or said at least one compound represents from 0.1% to 80% by weight, relative to the total weight of the composition.

22. The composition claim 21, wherein said at least one semi-crystalline polymer and/or said at least one compound represents from 0.5% to 40% by weight, relative to the total weight of the composition.

23. The composition claim 22, wherein said at least one semi-crystalline polymer and/or said at least one compound is present in an amount greater than 10% by weight, relative to the total weight of the composition.

24. The composition of claim 1, wherein the at least one semi-crystalline polymer is present in a weight ratio, relative to said at least one compound, ranging from 90:10 to 10:90.

25. The composition of claim 24, wherein said weight ratio ranges from 40:60 to 60:40.

26. The composition of claim 1, wherein the liquid fatty phase is present in an amount ranging from 5% to 99% by weight, relative to the total weight of the composition.

27. The composition of claim 1, wherein the liquid fatty phase is present in an amount ranging from 20% to 80% by weight, relative to the total weight of the composition.

28. The composition of claim 27, wherein the liquid fatty phase comprises at least one hydrocarbonaceous oil chosen from mineral and synthetic origin oils.

29. The composition of claim 1, wherein said composition is for caring for and/or treating and/or making up keratinous substances.

30. The composition of claim 1, further comprising at least one coloring material.

31. The composition of claim 30, wherein said at least one coloring material is chosen from lipophilic dyes, hydrophilic dyes, pigments, and pearlescent agents.

32. The composition of claim 30, wherein said at least one coloring material is present in an amount ranging from 0.01% to 50% by weight, relative to the total weight of the composition.

33. The composition of claim 32, wherein said at least one coloring material is present in an amount ranging from 5% to 30% by weight, relative to the total weight of the composition.

34. The composition of claim 31, wherein said pigments and pearlescent agents are provided in the form of a pigmentary paste.

35. The composition of claim 1, further comprising at least one additive chosen from mattifying fillers, water, antioxidants, essential oils preservatives, neutralizing agents, fragrances, waxes, and pasty fatty substances.

36. The composition of claim 35, wherein said at least one additive is chosen from waxes and is present in an amount ranging from greater than 0% to less than 10% by weight, relative to the total weight of the composition, and wherein said at least one additive is further chosen from mattifying fillers in an amount ranging from greater than 0% to less than 5% by weight, relative to the total weight of said composition.

37. The composition of claim 1, wherein the liquid fatty phase represents the continuous phase of the composition.

38. The composition of claim 1, wherein the ratio by weight of semi-crystalline polymer with an organic structure to the liquid fatty phase ranges from 0.20:1 to 0.50:1.

39. The composition of claim 38, wherein said ratio ranges from 0.25:1 to 0.45:1.

40. The composition of claim 1, wherein said composition is in anhydrous form.

41. The composition of claim 1, wherein said composition is in cast form.

42. The composition of claim 1, wherein said composition is in a form chosen from mascaras, eyeliners, foundations, lipsticks, deodorants, products for making up the body, eyeshadows, face powders, and concealers.

43. A lipstick comprising at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, and at least one compound chosen from crystalline and semi-crystalline compounds having organic structure and high melting point, wherein said compound is solid at ambient temperature and has a melting temperature of at least equal to 50° C., wherein said at least one semi-crystalline polymer has a number-average molecular mass of greater than 2,000, and wherein the liquid fatty phase and the at least one semi-crystalline polymer form a physiologically acceptable medium for the lips.

44. The lipstick of claim 43, wherein the at least one compound is chosen from second semi-crystalline polymers, wherein each of said second semi-crystalline polymers comprises i) a polymer backbone, and ii) at least one crystallizable organic side chain and/or one crystallizable organic block forming part of the backbone of the said second semi-crystalline polymer, and further wherein each of said second semi-crystalline polymers has a number-average molecular mass of greater than 2,000.

45. A process for caring for, making up, or treating a keratinous substance of a human being, comprising applying an effective amount of the composition of claim 1 to said keratinous substance.

46. A process for structuring, in the absence of wax and/or filler, a composition comprising a physiologically acceptable medium comprising at least one continuous liquid fatty phase, said process comprising including in said continuous liquid fatty phase an effective amount of at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, and at least one compound chosen from crystalline and semi-crystalline compounds having organic structure and high melting point, wherein said compound is solid at ambient temperature and has a melting temperature of at least equal to 50° C.,
wherein said at least one semi-crystalline polymer has a number-average molecular mass of greater than 2,000, and
wherein said composition is in solid form with a hardness ranging from 100 to 350 gf.

47. A processing for structuring, in the absence of wax and/or filler, a composition comprising a physiologically acceptable medium comprising at least one continuous liquid fatty phase, said process comprising including in said continuous liquid fatty phase a sufficient amount of at least one semi-crystalline polymer having an organic structure and a high melting point, wherein said semi-crystalline polymer is solid at ambient temperature, and has a melting temperature at least equal to 50° C., said at least one semi-crystalline polymer comprising i) a polymer backbone; and ii) at least one crystallizable organic side chain and/or at least one crystallizable organic block that forms part of the backbone of said at least one semi-crystalline polymer having a high melting point; and at least one compound chosen from crystalline and semi-crystalline compounds having organic structure and high melting point, wherein said compound is solid at ambient temperature and has a melting temperature of at least equal to 50° C.,
wherein said at least one semi-crystalline polymer has a number-average molecular mass of greater than 2,000,
and wherein said composition is in solid form and has a hardness ranging from 100 to 350 gf.

48. A process for structuring a composition comprising a physiologically acceptable medium comprising a liquid fatty phase, said process comprising including in said composition an effective amount of at least one semi-crystalline polymer having a low melting point and an organic structure, wherein said at least one semi-crystalline polymer is solid at ambient temperature and has a melting temperature of less than 50° C., and comprises a) a polymer backbone; and b) at least one crystallizable organic side chain and/or at least one crystallizable organic block that forms part of the backbone of said at least one semi-crystalline polymer with a low melting point, and at least one compound chosen from crystalline and semi-crystalline compounds having organic structure and high melting point, wherein said compound is solid at ambient temperature and has a melting temperature of at least equal to 50° C.,
wherein said at least one semi-crystalline polymer has a number-average molecular mass of greater than 2,000,
and wherein said liquid fatty phase is in solid form and is at least one of glossy, nonsticky, and covering.

49. The process of claim 48, further comprising including in said composition at least one second semi-crystalline polymer having an organic structure and a high melting point, wherein said second polymer is solid at ambient temperature, has a melting temperature at least equal to 50° C., and comprises i) a polymer backbone; and ii) at least one crystallizable organic side chain and/or at least one crystallizable organic block that forms part of the backbone of said second polymer, wherein said second at least one semi-crystalline polymer has a number-average molecular mass of greater than 2,000.

50. A method of making a glossy and/or nonsticky and/or covering cosmetic composition comprising including in said composition at least one first semi-crystalline polymer having a low melting point and an organic structure, wherein said at least one first polymer is solid at ambient temperature, has a melting temperature of less than 50° C., and comprises a) a polymer backbone; and b) at least one crystallizable organic side chain and/or at least one crystallizable organic block that forms part of the backbone of said at least one first semi-crystalline polymer, and at least one compound chosen from crystalline and semi-crystalline compounds having organic structure and high melting point, wherein said compound is solid at ambient temperature and has a melting temperature of at least equal to 50° C., wherein said at least one first semi-crystalline polymer has a number-average molecular mass of greater than 2,000, and at least one second semi-crystalline polymer having an organic structure and a high melting point, wherein said at least one second semi-crystalline polymer is solid at ambient temperature, has a melting temperature at least equal to 50° C., and comprises i) a polymer backbone; and ii) at least one crystallizable organic side chain and/or at least one crystallizable organic block that forms part of the backbone of said at least one second semi-crystalline polymer, wherein said at least one second semi-crystalline polymer has a number-average molecular mass of greater than 2,000.

51. The process of claim 46, wherein the weight ratio of the at least one semi-crystalline polymer having an organic structure to the liquid fatty phase ranges from 0.20:1 to 0.50:1.

52. The process of claim 51, wherein said weight ratio ranges from 0.25:1 to 0.45:1.

53. A composition comprising:
at least one liquid fatty phase structured by at least one semi-crystalline polymer having a low melting point and an organic structure, wherein said at least one semi-crystalline polymer is solid at ambient temperature and has a melting temperature of less than 50° C., and wherein said at least one semi-crystalline polymer comprises (a) a polymer backbone; and (b) at least one crystallizable organic side chain and/or at least one crystallizable organic block which forms part of the polymer backbone of said semi-crystalline polymer, and at least one compound chosen from crystalline and semi-crystalline compounds having an organic structure and a high melting point, wherein said compound is solid at ambient temperature and has a melting temperature of at least equal to 50° C., wherein said at least one semi-crystalline polymer has a number-average molecular mass of greater than 2,000, and wherein the liquid fatty phase and the at least one semi-crystalline polymer form a physiologically acceptable medium; and wherein said semi-crystalline polymer does not comprise a polysaccharide backbone.

* * * * *

UNITED STATES PATENT AND TRADEMARK OFFICE
CERTIFICATE OF CORRECTION

PATENT NO. : 6,949,504 B2 Page 1 of 1
DATED : September 27, 2005
INVENTOR(S) : Jean Mondet et al.

It is certified that error appears in the above-identified patent and that said Letters Patent is hereby corrected as shown below:

<u>Column 25,</u>
Line 35, "A processing" should read -- A process --.

Signed and Sealed this

Twenty-seventh Day of December, 2005

JON W. DUDAS
*Director of the United States Patent and Trademark Office*